US00PP15754P3

(12) United States Plant Patent
Redman

(10) Patent No.: US PP15,754 P3
(45) Date of Patent: May 10, 2005

(54) *CHRYSANTHEMUM* PLANT NAMED 'CHISEL TIME PINK'

(50) Latin Name: *Chrysanthemum morifolium*
Varietal Denomination: Chisel Time Pink

(75) Inventor: Ruth Redman, Bognor Regis (GB)

(73) Assignee: Cleangro LTD (GB)

( * ) Notice: Subject to any disclaimer, the term of this patent is extended or adjusted under 35 U.S.C. 154(b) by 172 days.

(21) Appl. No.: 10/364,251

(22) Filed: Feb. 10, 2003

(65) Prior Publication Data

US 2004/0158897 P1 Aug. 12, 2004

(51) Int. Cl.[7] ..... A01H 5/00

(52) U.S. Cl. ..... Plt./286

(58) Field of Search ..... Plt./286

(56) References Cited

PUBLICATIONS

Chrysanthemum Breeders Association (CBA) 2000 Catalogue pages listing *Chrysanthemum* variety 'Scott' on second page.
1998 Ficor Catalog listing *Chrysanthemum* 'Kiku Time' variety. See, e.g., p. 4.
1999 Ficor Catalog listing *Chrysanthemum* 'Kiku Time' variety. See, e.g., p. 4.
Royal Van Zanten Catalog 2003 listing showing the commercially available variety 'Scott,' as "USPP pend" on the third line up from the bottom of the attached page from the catalog.

*Primary Examiner*—Anne Marie Grunberg
(74) *Attorney, Agent, or Firm*—Howrey Simon Arnold & White, LLP

(57) ABSTRACT

A new variety of *Chrysanthemum* plant named 'Chisel Time Pink,' having a good uniform canopy of white quill single flowers with pink spoon tips and a light green disc. The new variety has a medium tall vigor, free branching, uniform spreading habit and good foliage presentation.

1 Drawing Sheet

Latin name of the genus and species: Botanical classification: *Chrysanthemum morifolium.*

Variety denomination: The new *Chrysanthemum* variety denomination is 'Chisel Time Pink.'

BACKGROUND OF THE INVENTION

The present invention comprises a new and distinct cultivar of *Chrysanthemum* botanically known as *Chrysanthemum morifolium*, and referred to by the cultivar name 'Chisel Time Pink.'

'Chisel Time Pink,' identified as 21033-0, originated from a cross made in a controlled breeding program in Chichester, West Sussex, United Kingdom. The female parent of the new variety is an undistributed, unpatented seedling identified as P381D4. The male parent of the new variety is an undistributed, unpatented seedling identified as 20398-0 of the unpatented variety known as 'Kiku Time.' The new variety 'Chisel Time Pink' has been asexually reproduced by vegetative cuttings in Chichester, West Sussex, United Kingdom, and the distinguishing characteristics are retained through successive generations of asexual reproduction.

BRIEF SUMMARY OF THE INVENTION

'Chisel Time Pink' is a Pot type of *Chrysanthemum* plant variety having white single quill flowers with pink spoon tips.

Comparison with Female Parent

Plants of the new *Chrysanthemum* variety 'Chisel Time Pink' are dissimilar to the female parent 'P381D4' in plant habitat and growth rate. In side-by-side comparisons in Chichester, West Sussex, United Kingdom, under commercial practice, plants of the new *Chrysanthemum* variety 'Chisel Time Pink' differed from plants of the parent 'P381D4' in the following characteristics.

1. The new variety 'Chisel Time Pink' produces a white quill with a pink spoon tip flower whereas the parent 'P381D4' produces red single flowers.
2. Plants of the new variety 'Chisel Time Pink' have larger and taller inflorescence than plants of the parent 'P381D4.'

Comparison with Male Parent

Plants of the new *Chrysanthemum* variety 'Chisel Time Pink' are dissimilar to the male parent 'Kiku Time' in plant habitat and growth rate. In side-by-side comparisons in Chichester, West Sussex, United Kingdom, under commercial practice, plants of the new *Chrysanthemum* variety 'Chisel Time Pink' differed from plants of the parent 'Kiku Time' in the following characteristics.

1. The new variety 'Chisel Time Pink' produces a white quill with a pink spoon tip flower whereas the parent 'Kiku Time' produces red single flowers.
2. Plants of the new variety 'Chisel Time Pink' have larger and taller inflorescence than plants of the parent 'Kiku Time.'

Comparison with Other Varieties

The plants of the new variety 'Chisel Time Pink' are similar to 'Scott' (U.S. Plant Pat. No. 14,155) in plant habit and growth rate. However, in side by side comparisons in Chichester, West Sussex, United Kingdom, under commercial practice, plants of the new *Chrysanthemum* variety 'Chisel Time Pink' differed from plants of 'Scott' in the following characteristics.

1. The new variety 'Chisel Time Pink' produces a white quill with a pink spoon tip flowers whereas 'Scott' produces purple spoon tip flowers.
2. The plants of the new variety 'Chisel Time Pink' have larger and taller inflorescence than plants of 'Scott.'

BRIEF DESCRIPTION OF ILLUSTRATIONS

Typical specimens of the plant and flowers for the new *Chrysanthemum* variety 'Chisel Time Pink' are shown in the accompanying digital photograph. The colors shown are as true as possible within the usual limits of this kind of illustration. FIG. 1 is a whole plant view of the new variety 'Chisel Time Pink' grown in a pot. The plant shown in the illustration is 55 days from the commencement of Short Days.

DETAILED BOTANICAL DESCRIPTION

The following description of the new *Chrysanthemum* variety 'Chisel Time Pink' is of plants grown in a greenhouse in Chichester, West Sussex, United Kingdom, in the month of May. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5000 to 6000 foot candles. The plants respond well to the use of growth retardant, such as three B9 treatments at about 2 g per liter. To produce a commercial product the plants may be pinched once with the center bud removed. The typical container size for commercial growth is 1 liter. It has been observed that the shelf life of the new variety is about 21 days with a response time of about 7 weeks. The new variety is suitable for growth in a temperature range of 15° C. to 25° C.

The following description is with respect to a plant produced as a pot *Chrysanthemum.* In the description of this new *Chrysanthemum* variety, color values have been taken from The Royal Horticultural Society Colour Chart (R.H.S.C.C.).

PLANT

Plant type: Pot.
Habit: Upright.
Height: 21 cm.
Width: 30 cm.
Branching characteristics: Upright spreading.
Length of lateral branches: 16 cm.
Number of breaks from pinch: 4.
Stem Color: 137C.
Response Time: 7 weeks.
Vigor: Medium tall.
Shelf Life: Near 21 days.
Disease (susceptability/resistance observed): None observed to date.
Pest (susceptability/resistance observed): None observed to date.
Growth retardant type and treatment: 3 applications of 2.5 gm/liter B9@2, 21 and 28 days after sticking of unrooted cuttings.
The plants were grown for 2 weeks in Long Day conditions (20 hours of light) and then transferred to Short Day conditions (13 hours of dark).
Propagation:
*Type.*—Vegetative propagation via stem cuttings.
*Time to rooting.*—14 days with soil temperatures of 18° C.
*Rooting habit.*—After 7 Long Days first roots emerge form root primordia. In 14 Long Days a complete root system is developed.

FOLIAGE

Number of leaves per lateral branch: 9.
Compound or single: Single.
Arrangement of leaves: Alternate.
*Shape of leaf.*—Typically 5 lobed ovate.
*Size of leaf.*—Width (cm): 5.5 Length (cm): 8.5.
*Leaf apex.*—Acute.
*Base.*—Obtuse.
*Attachment.*—Petioled.
*Aspect.*—Slight undulating.
*Margin.*—Palmately lobed.
*Surface characteristics.*—Top: slightly pubescent. Bottom: slightly pubescent.
Petiole:
*Color.*—137D.
*Length.*—1.5 cm.
Venation: Net prominent mid-vein at underside.
*Color.*—Upper side: near 137D under side: near 138B.
Color:
*Mature leaf.*—Upper side: near 137A under side: near 137D.
*Young Leaf.*—Upper side; near 137C under side: near 137D.

FLOWER

Flower appearance: Matte.
Flower type: Single.
Flower form: Cupped.
Flower shape: Round.
Flowering habit: Cyme.
Number of blossoms per branch: 7.
Inflorescence form: Cyme.
*Depth of fully expanded blossoms.*—2 cm.
*Diameter of fully expanded blossoms.*—8 cm.
Phyllaries:
*Number.*—20–25.
*Color.*—Near 137D.
*Length.*—0.7 to 1.1 cm.
*Width.*—0.2 to 0.4 cm.
*Texture/appearance.*—Pubescent.
Peduncle: Peduncle length is shortest at the terminal flower and progressively longer moving down the stem.
*Length.*—10 cm.
*Color.*—Near 137D.
*Surface.*—Pubescent.
*Habit.*—Slightly undulating.
*Strength.*—Medium.
Pedicel:
*Length.*—Terminal: 2 cm; lateral: 3 cm.
*Color.*—Near 137D.
*Surface.*—Pubescent.
*Habit.*—Slightly undulating.
*Strength.*—Medium.

Ray florets:
*Form/shape*.—Straight and cylindrical.
*Texture/appearance*.—Matte.
*Number per flower*.—38.
*Length*.—3.5 cm; Width: 0.2 cm.
*Apex*.—Rounded.
*Base*.—Tapered.
*Margin*.—Entire.

Disc florets:
*Form/shape*.—Cylindric.
*Texture/appearance*.—Shiny.
*Number per flower*.—135.
*Length*.—0.6 cm; Width: 0.1 cm.
*Diameter of disc*.—1.5 cm.

Fragrance: None.

Flower bud (at onset of color):
*Length*.—1.5 cm.
*Diameter*.—1.2 cm.
*Form/shape*.—Spherical.

General flower color:
1. *Ray florets, upper side*.—Immature: near 61B. Mature: near 63A. Older/fading: near 63B.
2. *Ray florets, under side*.—Immature: near 66C. Mature: near 65A. Older/fading: near 65C.
3. *Disc florets*.—Immature: near 144A. Mature: near 5A. Older/fading: near 5C.
4. *Bud*.—63A.

Flower progression with age: flower form does not change but there is a little color fading with age.

REPRODUCTIVE ORGANS

Gynoecium: Present on Ray and Disc florets.

Ray florets per individual flower:
*Pistil number*.—38.
*Stigma color*.—Near 9B.
*Stigma shape*.—Forked.
*Style color*.—Near 154B.
*Style length*.—0.4 cm.

Disc florets per individual flower:
*Pistil number*.—135.
*Stigma color*.—Near 154A.
*Stigma shape*.—Forked.
*Style color*.—Near 154B.
*Style length*.—0.4 cm.

Androecium: Present on Disc florets only.
*Stamen number*.—135.
*Anther shape*.—Forked.
*Anther color*.—Near 150C.
*Pollen color*.—Near 14A.
*Pollen quantity*.—Abundant.

Fruit and Seeds: None observed.

What is claimed is:

1. A new and distinct variety of *Chrysanthemum* plant, substantially as described and illustrated herein.

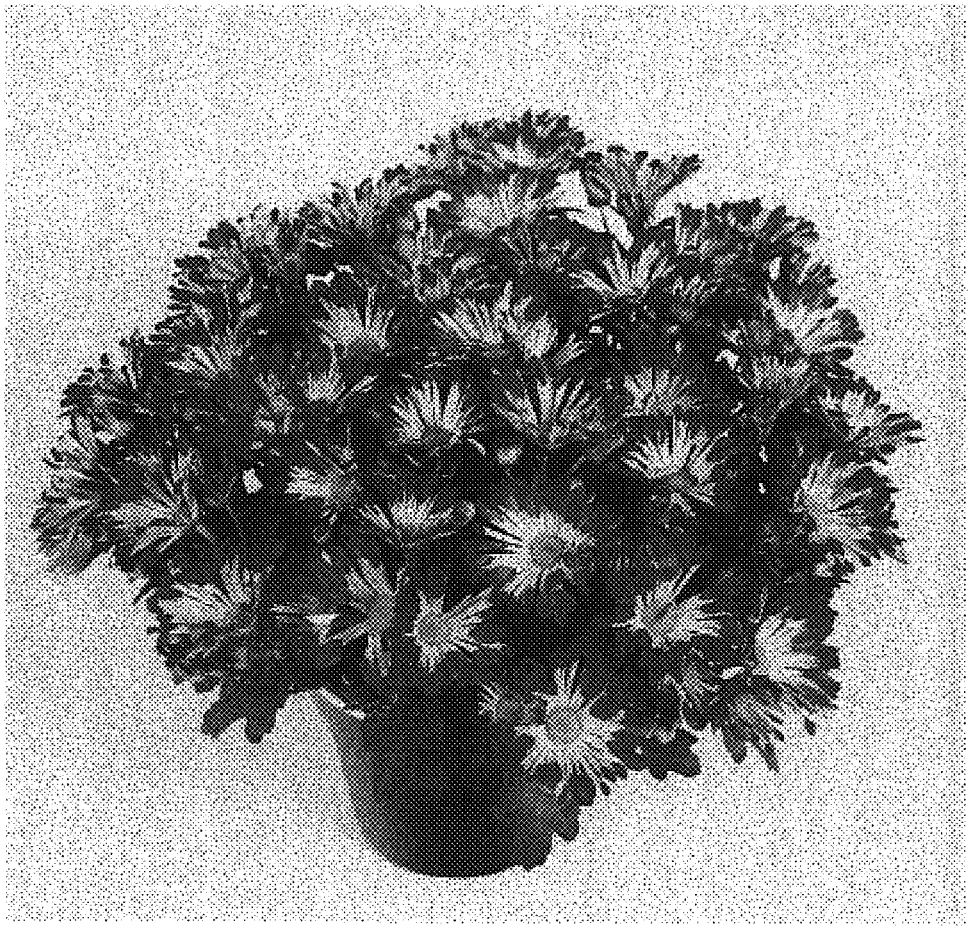

* * * * *